(12) United States Patent
Burkamp et al.

(10) Patent No.: US 7,449,585 B2
(45) Date of Patent: Nov. 11, 2008

(54) INDAZOL-3-ONES AND ANALOGUES AND DERIVATIVES THEREOF WHICH MODULATE THE FUNCTION OF THE VANILLOID-1 RECEPTOR (VR1)

(75) Inventors: Frank Burkamp, Bishops Stortford (GB); Stephen Robert Fletcher, Bishops Stortford (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 194 days.

(21) Appl. No.: 10/579,355

(22) PCT Filed: Nov. 12, 2004

(86) PCT No.: PCT/GB2004/004809

§ 371 (c)(1),
(2), (4) Date: May 12, 2006

(87) PCT Pub. No.: WO2005/049601

PCT Pub. Date: Jun. 2, 2005

(65) Prior Publication Data

US 2007/0129374 A1  Jun. 7, 2007

(30) Foreign Application Priority Data

Nov. 14, 2003  (GB) .................. 0326633.5

(51) Int. Cl.
| | |
|---|---|
| C07D 231/56 | (2006.01) |
| C07D 471/02 | (2006.01) |
| C07D 487/00 | (2006.01) |
| A61K 31/415 | (2006.01) |
| A61K 31/44 | (2006.01) |
| A61K 241/36 | (2006.01) |
| A61K 31/495 | (2006.01) |

(52) U.S. Cl. ................. 548/361.5; 548/362.1; 546/118; 546/120; 544/350; 544/355; 514/405; 514/303; 514/249

(58) Field of Classification Search ............. 548/361.5, 548/362.1; 514/249, 405, 303; 546/118, 546/120; 544/350, 355
See application file for complete search history.

(56) References Cited

FOREIGN PATENT DOCUMENTS

WO  WO 03/055484 A  7/2003

OTHER PUBLICATIONS

Lee, J. et al., "N-(3-Acyloxy-2-Benzylpropyl)-N'-Dihydroxy tetrahydrobenzazepine and Tetrahydroisoquinoline Thiourea Analogues as Vanilloid Receptor Ligands", Bioorganic & Medicinal Chemistry, Elsevier Science Ltd, vol. 9, 2001, pp. 1713-1720.

*Primary Examiner*—Kamal Saeed
*Assistant Examiner*—Kristin Bianchi
(74) *Attorney, Agent, or Firm*—Sylvia A. Ayler; William Krovatin

(57) ABSTRACT

Compounds of formula (I), which are useful as therapeutic compounds, particularly in the treatment of pain and other conditions ameliorated by the modulation of the function of the vanilloid-1 receptor (VR1).

(I)

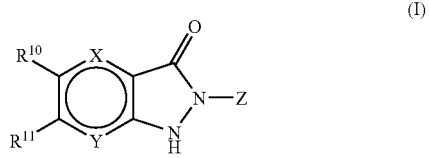

5 Claims, No Drawings

INDAZOL-3-ONES AND ANALOGUES AND DERIVATIVES THEREOF WHICH MODULATE THE FUNCTION OF THE VANILLOID-1 RECEPTOR (VR1)

CROSS REFERENCE TO RELATED APPLICATIONS

This application claims the benefit of Great Britain Provisional Application No. 0326633.5 filed Nov. 14, 2003 and PCT/GB04/004809 filed Nov. 12, 2004.

The present invention is concerned with 1,2-dihydro-2-(para-substituted aryl/heteroaryl)-5 or 6-aryl/heteroaryl-3H-indazol-3-ones and analogues and derivatives thereof as well as pharmaceutically acceptable salts and prodrugs thereof, which are useful as therapeutic compounds, particularly in the treatment of pain and other conditions ameliorated by the modulation of the function of the vanilloid-1 receptor (VR1).

The pharmacologically active ingredient of chilli peppers has been recognised for some time to be the phenolic amide capsaicin. The application of capsaicin to mucous membranes or when injected intradermally, causes intense burning-like pain in humans. The beneficial effects of topical administration of capsaicin as an analgesic is also well established. However, understanding of the underlying molecular pharmacology mediating these responses to capsaicin has been a more recent development.

The receptor for capsaicin, termed the vanilloid VR1 receptor, was cloned by Caterina and colleagues at UCSF in 1997 (Nature, 398:816, 1997). VR1 receptors are cation channels that are found on sensory nerves that innervate the skin, viscera, peripheral tissues and spinal cord. Activation of VR1 elicits action potentials in sensory fibres that ultimately generate the sensation of pain. Importantly the VR1 receptor is activated not only by capsaicin but also by acidic pH and by noxious heat stimuli. It is also sensitized by a number of inflammatory mediators and thus appears to be a polymodal integrator of painful stimuli.

The prototypical VR1 antagonist is capsazepine (Walpole et al, *J. Med. Chem.*, 37:1942, 1994)—VR1 $IC_{50}$ of 420 nM. A novel series of sub-micromolar antagonists has also been reported recently (Lee et al, *Bioorg. Med. Chem.*, 9:1713, 2001), but these reports provide no evidence for in vivo efficacy. A much higher affinity antagonist has been derived from the 'ultra-potent' agonist resiniferatoxin. Iodo-resiniferatoxin (Wahl et al., *Mol. Pharmacol*, 59:9, 2001) is a nanomolar antagonist of VR1 but does not possess properties suitable for an oral pharmaceutical. This last is also true of the micromolar peptoid antagonists described by Garcia-Martinez (*Proc. Natl. Acad. Sci., USA*, 99:2374, 2002). Most recently International (PCT) patent publication No. WO 02/08221 has described a novel series of VR1 antagonists, which are stated to show efficacy in a number of animal models. We herein describe another novel series of VR1 modulators. These comprise predominantly VR1 antagonists but encompass VR1 partial antagonists and VR1 partial agonists. Such compounds have been shown to be efficacious in animal models of pain.

The present invention provides compounds of formula (I):

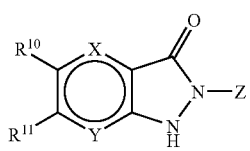
(I)

wherein X and Y are each $CR^1$ or N;
one of $R^{10}$ and $R^{11}$ is $R^1$ and the other is W;
each $R^1$ is hydrogen, halogen, hydroxy, cyano, amino, $C_{1-4}$alkyl, $C_{1-4}$alkoxy, halo$C_{1-4}$alkyl or halo$C_{1-4}$alkoxy;
W is a phenyl ring or a six-membered heteroaromatic ring containing one, two or three nitrogen atoms, which ring is optionally substituted by halogen, $C_{1-6}$alkyl, $C_{2-6}$alkenyl, $C_{2-6}$alkynyl, $C_{1-6}$alkoxy, cyano, nitro, amino, $C_{1-6}$alkylamino, di($C_{1-6}$alkyl)amino, halo$C_{1-6}$alkyl, halo$C_{1-6}$alkoxy, carboxy, hydroxy$C_{1-6}$alkyl or amino$C_{1-6}$alkyl; and
Z is a phenyl ring or a six-membered heteroaromatic ring containing one, two or three nitrogen atoms, which ring is substituted at least at the position para to the attachment of the ring to the rest of the molecule by halogen, $C_{1-6}$alkyl, $C_{2-6}$alkenyl, $C_{2-6}$alkynyl, $C_{1-6}$alkoxy, cyano, nitro, amino, $C_{1-6}$alkylamino, di($C_{1-6}$alkyl)amino, halo$C_{1-6}$alkyl, halo$C_{1-6}$alkoxy, carboxy, hydroxy$C_{1-6}$alkyl or amino$C_{1-6}$alkyl;
or a pharmaceutically acceptable salt thereof.

$R^1$ is preferably hydrogen, halogen, hydroxy, cyano, amino, $C_{1-2}$alkyl, $C_{1-2}$alkoxy, halo$C_{1-2}$alkyl or halo$C_{1-2}$alkoxy. $R^1$ is more preferably fluorine, methyl or hydrogen. $R^1$ is generally hydrogen.

X and Y are generally $CR^1$.

W is preferably unsubstituted or substituted by one, two or three substituents independently chosen from halogen, $C_{1-2}$alkyl, $C_{1-2}$alkoxy, cyano, nitro, amino, $C_{1-2}$alkylamino, di($C_{1-2}$alkyl)amino, halo$C_{1-2}$alkyl, halo$C_{1-2}$alkoxy, hydroxy$C_{1-2}$alkyl or amino$C_{1-2}$alkyl. More preferably W is optionally substituted by hydrogen, $C_{1-2}$alkyl, $C_{1-2}$alkoxy, halo$C_{1-2}$alkyl or halo$C_{1-2}$alkoxy. Most preferably the optional substituent is trifluoromethyl, methyl or methoxy. W is preferably monosubstituted. W preferably possesses a substituent at the position ortho to the point of attachment to the rest of the molecule. W is most preferably monosubstituted at the position ortho to the point of attachment to the rest of the molecule.

W is preferably a phenyl or pyridyl ring. Particular embodiments of W are 3-trifluoromethylpyrid-2-yl, 3-methylpyrid-2-yl and 2-methoxyphenyl.

Z is preferably substituted by one or two substituents independently chosen from halogen, $C_{1-2}$alkyl, $C_{1-2}$alkoxy, cyano, nitro, amino, $C_{1-2}$alkylamino, di($C_{1-2}$alkyl)amino, halo$C_{1-2}$alkyl, halo$C_{1-2}$alkoxy, hydroxy$C_{1-2}$alkyl and amino$C_{1-2}$alkyl. More preferably Z is substituted by halogen, methyl, trifluoromethyl, methoxy or trifluoromethoxy. Most preferably Z is substituted by trifluoromethyl. Z may be monosubstituted. Z may be monosubstituted by trifluoromethyl. Z is preferably a substituted phenyl or pyridyl, especially a substituted phenyl. An embodiment of Z is 4-trifluoromethylphenyl.

Preferably $R^{10}$ is $R^1$ and $R^{11}$ is W.

A subset of compounds of the present invention is represented by formula IA:

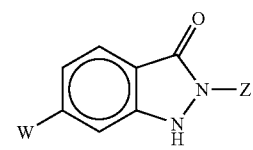
(IA)

in which W is phenyl or pyridyl optionally substituted by halogen, $C_{1-2}$alkyl, $C_{1-2}$alkoxy, halo$C_{1-2}$alkyl or halo$C_{1-2}$alkoxy; and Z is phenyl or pyridyl substituted at the position para to the point of attachment to the rest of the molecule by halogen, $C_{1-2}$alkyl, $C_{1-2}$alkoxy, halo$C_{1-2}$alkyl or halo$C_{1-2}$alkoxy;

or a pharmaceutically acceptable salt thereof.

W is preferably substituted at a position ortho to the point of attachment to the rest of the molecule. W is preferably monosubstituted. The substituent on W is preferably trifluoromethyl, methyl, trifluoromethoxy or methoxy. W is most preferably methyl, trifluoromethyl or methoxy.

Z is preferably substituted by fluorine, methyl, methoxy, trifluoromethyl or trifluoromethoxy. Z is preferably trifluoromethyl. Z is preferably a substituted phenyl.

Particular embodiments of the invention include:
1,2-dihydro-2-(4-trifluoromethylphenyl)-6-(3-trifluoromethyl-2-pyridinyl)-3H-indazol-3-one;
1,2-dihydro-6-(3-methyl-2-pyridinyl)-2-(4-trifluoromethylphenyl)-3H-indazol-3-one;
1,2-dihydro-2-(4-trifluoromethylphenyl)-5-(3-trifluoromethyl-2-pyridinyl)-3H-indazol-3-one;
1,2-dihydro-6-(2-methoxyphenyl)-2-(4-trifluoromethylphenyl)-3H-indazol-3-one; and
1,2-dihydro-6-(3-methyl-2-pyridinyl)-2-(4-trifluoromethylphenyl)-3H-pyrazolo[3,4-b]pyridin-3-one;

or a pharmaceutically acceptable salt thereof.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the term "hydroxy$C_{1-6}$alkyl" means a $C_{1-6}$alkyl group in which one or more (in particular 1 to 3, and especially 1) hydrogen atoms have been replaced by hydroxy groups. Particularly preferred are hydroxy$C_{1-3}$alkyl groups, for example, $CH_2OH$, $CH_2CH_2OH$, $CH(CH_3)OH$ or $C(CH_3)_2OH$, and most especially $CH_2OH$. "Aminoalkyl" shall be construed in an analogous manner.

As used herein, the terms "halo$C_{1-6}$alkyl" and "halo$C_{1-6}$alkoxy" means a $C_{1-6}$alkyl or $C_{1-6}$alkoxy group in which one or more (in particular, 1 to 3) hydrogen atoms have been replaced by halogen atoms, especially fluorine or chlorine atoms. Preferred are fluoro$C_{1-6}$alkyl and fluoro$C_{1-6}$alkoxy groups, in particular, fluoro$C_{1-3}$alkyl and fluoro$C_{1-3}$alkoxy groups, for example, $CF_3$, $CH_2CH_2F$, $CH_2CHF_2$, $CH_2CF_3$, $OCF_3$, $OCH_2CH_2F$, $OCH_2CHF_2$ or $OCH_2CF_3$, and most especially $CF_3$ and $OCF_3$.

As used herein, the terms "alkenyl" and "alkynyl" as a group or part of a group means that the group is straight or branched. Examples of suitable alkenyl groups include vinyl and allyl. A suitable alkynyl group is acetylene or propargyl.

When used herein, the term "halogen" means fluorine, chlorine, bromine and iodine. The most preferred halogens are fluorine and chlorine, especially fluorine.

Examples of 6-membered heterocycles are pyridine, pyrimidine, pyrazine, pyridazine and triazine.

In a further aspect of the present invention, the compounds of formula I may be prepared in the form of a pharmaceutically acceptable salt, especially an acid addition salt.

For use in medicine, the salts of the compounds of formula I will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. A further salt is the acid addition salt with benzenesulfonic acid. Preferred pharmaceutically acceptable salts of the compounds of the present invention are the besylate salts. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the compound of formula I with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention also includes within its scope N-oxides of the compounds of formula I above. In general, such N-oxides may be formed on any available nitrogen atom. The N-oxides may be formed by conventional means, such as reacting the compound of formula I with oxone in the presence of wet alumina.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula I and salts thereof, for example, hydrates.

The compounds according to the invention may have one or more asymmetric centres, and may accordingly exist both as enantiomers and as diastereoisomers. It is to be understood that all such isomers and mixtures thereof are encompassed within the scope of the present invention. Furthermore, the compounds of formula I may also exist in tautomeric forms and the invention includes within its scope both mixtures and separate individual tautomers.

The present invention further provides pharmaceutical compositions comprising one or more compounds of formula I in association with a pharmaceutically acceptable carrier or excipient.

Preferably the compositions according to the invention are in unit dosage forms such as tablets, pills, capsules, powders, granules, sterile parenteral solutions or suspensions, metered aerosol or liquid sprays, drops, ampoules, auto-injector devices, suppositories, creams or gels; for oral, parenteral, intrathecal, intranasal, sublingual, rectal or topical administration, or for administration by inhalation or insufflation.

Oral compositions such as tablets, pills, capsules or wafers are particularly preferred. For preparing solid compositions such as tablets, the principal active ingredient is mixed with a pharmaceutical carrier, e.g. conventional tabletting ingredients such as corn starch, lactose, sucrose, sorbitol, talc, stearic acid, magnesium stearate, dicalcium phosphate or gums, and other pharmaceutical diluents, e.g. water, to form a solid pre-formulation composition containing a homogeneous mixture of a compound of the present invention, or a pharmaceutically acceptable salt thereof. When referring to these pre-formulation compositions as homogeneous, it is meant that the active ingredient is dispersed evenly throughout the composition so that the composition may be readily subdivided into equally effective unit dosage forms such as tablets, pills and capsules. This solid pre-formulation composition is then subdivided into unit dosage forms of the type described above containing from 0.1 to about 500 mg of the active ingredient of the present invention. Favoured unit dosage forms contain from 1 to 500 mg, for example 1, 5, 10, 25, 50, 100, 300 or 500 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of painful conditions such as those listed below, a suitable dosage level is about 1.0 mg to 15 g per day, preferably about 5.0 mg to 1 g per day, more preferably about 5 mg to 500 mg per day, especially 10 mg to 100 mg per day. The compounds may be administered on a regimen of 1 to 4 times per day.

It will be appreciated that the amount of a compound of formula I required for use in any treatment will vary not only with the particular compounds or composition selected but also with the route of administration, the nature of the condition being treated, and the age and condition of the patient, and will ultimately be at the discretion of the attendant physician.

The invention further provides a compound of formula I as defined above, or a pharmaceutically acceptable salt thereof, for use in treatment of the human or animal body. Preferably, said treatment is for a condition which is susceptible to treatment by modulation (preferably antagonism) of VR1 receptors.

The compounds of the present invention will be of use in the prevention or treatment of diseases and conditions in which pain and/or inflammation predominates, including chronic and acute pain conditions. Such conditions include rheumatoid arthritis; osteoarthritis; post-surgical pain; musculo-skeletal pain, particularly after trauma; spinal pain; myofascial pain syndromes; headache, including migraine, acute or chronic tension headache, cluster headache, temporomandibular pain, and maxillary sinus pain; ear pain; episiotomy pain; burns, and especially primary hyperalgesia associated therewith; deep and visceral pain, such as heart pain, muscle pain, eye pain, orofacial pain, for example, odontalgia, abdominal pain, gynaecological pain, for example, dysmenorrhoea, pain associated with cystitis and labour pain, chronic pelvic pain, chronic prostatitis and endometriosis; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; itching conditions including pruritus, itch due to hemodialysis, and contact dermatitis; pain (as well as broncho-constriction and inflammation) due to exposure (e.g. via ingestion, inhalation, or eye contact) of mucous membranes to capsaicin and related irritants such as tear gas, hot peppers or pepper spray; neuropathic pain conditions such as diabetic neuropathy, chemotherapy-induced neuropathy and post-herpetic neuralgia; "non-painful" neuropathies; complex regional pain syndromes; pain associated with carcinoma, often referred to as cancer pain; central nervous system pain, such as pain due to spinal cord or brain stem damage, low back pain, sciatica and ankylosing spondylitis; gout; scar pain; irritable bowel syndrome; inflammatory bowel disease; urinary incontinence including bladder detrusor hyper-reflexia and bladder hyper-sensitivity; respiratory diseases including chronic obstructive pulmonary disease (COPD), chronic bronchitis, cystic fibrosis, asthma and rhinitis, including allergic rhinitis such as seasonal and perennial rhinitis, and non-allergic rhinitis and cough; autoimmune diseases; and immunodeficiency disorders. The compounds of the present invention may also be used to treat depression. They may also be used to treat gastro-oesophageal reflux disease (GERD), particularly the pain associated with GERD.

Thus, according to a further aspect, the present invention provides a compound of formula (I) for use in the manufacture of a medicament for the treatment or prevention of physiological disorders that may be ameliorated by modulating VR1 activity.

The present invention also provides a method for the treatment or prevention of physiological disorders that may be ameliorated by modulating VR1 activity, which method comprises administration to a patient in need thereof of an effective amount of a compound of formula I or a composition comprising a compound of formula I.

According to a further or alternative aspect, the present invention provides a compound of formula I for use in the manufacture of a medicament for the treatment or prevention of a disease or condition in which pain and/or inflammation predominates.

The present invention also provides a method for the treatment or prevention of a disease or condition in which pain and/or inflammation predominates, which method comprises administration to a patient in need thereof of an effective amount of a compound of formula I or a composition comprising a compound of formula I.

According to a further aspect of the present invention, it may be desirable to treat any of the aforementioned conditions with a combination of a compound according to the present invention and one or more other pharmacologically active agents suitable for the treatment of the specific condition. The compound of formula I and the other pharmacologically active agent(s) may be administered to a patient simultaneously, sequentially or in combination. Thus, for example, for the treatment or prevention of pain and/or inflammation, a compound of the present invention may be used in conjunction with other analgesics, such as acetaminophen (paracetamol), aspirin and other NSAIDs, including selective cyclooxygenase-2 (COX-2) inhibitors, as well as opioid analgesics, especially morphine, NR2B antagonists, bradykinin antagonists, anti-migraine agents, anticonvulsants such as oxcarbazepine and carbamazepine, antidepressants (such as TCAs, SSRIs, SNRIs, substance P antagonists, etc.), spinal blocks, gabapentin, pregabalin and asthma treatments (such as $\theta_2$-adrenergic receptor agonists or leukotriene $D_4$antagonists (e.g. montelukast).

Specific anti-inflammatory agents include diclofenac, ibuprofen, indomethacin, nabumetone, ketoprofen, naproxen, piroxicam and sulindac, etodolac, meloxicam, rofecoxib, celecoxib, etoricoxib, parecoxib, valdecoxib and tilicoxib. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof. Suitable anti-migraine agents of use in conjunction with a compound of the present invention include CGRP-antagonists, ergotamines or 5-$HT_1$ agonists, especially sumatriptan, naratriptan, zolmatriptan or rizatriptan.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of a disease or condition in which pain and/or inflammation predominates.

The compounds of formula I can be made by reacting a compound of formula II with a compound of formula III:

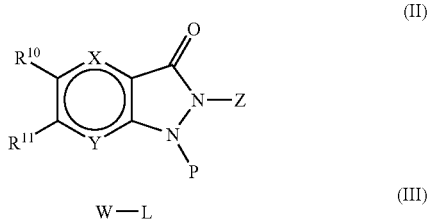

wherein W, X, Y and Z are as defined for formula I, P is hydrogen or a protecting group, one of $R^{10}$ and $R^{11}$ is $R^1$ as defined above and the other is $L^1$ and one of L and $L^1$ is Cl or $Sn(alkyl)_3$, for example $Sn(methyl)_3$ or $Sn(n-butyl)_3$, and the other is bromine or chlorine, followed, if necessary, by deprotecting the compound obtained. When L or $L^1$ is Cl it can be initially converted into a group $B(OH)_2$ under conditions suitable for a Suzuki Coupling Reaction (for review, see for instance A. Suzuki, Pure Appl. Chem., 1991, 63, 419-422), for example, in the presence of a palladium catalyst such as tetrakis(triphenylphosphine)palladium(0), tris(dibenzylideneacetone)dipalladium(0), (1,1'-bis(diphenylphosphino)ferrocene)dichloropalladium or dichloro-(1,4-bis(diphenylphosphino)butane)palladium, in a suitable solvent such as an ether, for example, dimethoxyethane or dioxane or an aromatic hydrocarbon, for example toluene, at an elevated temperature and in the presence of a base such as sodium carbonate. Where L or $L^1$ is $Sn(alkyl)_3$, the reaction is conveniently effected under conditions suitable for a Stille Coupling Reaction (for review, see for instance J. K. Stille, Angew. Chem. Int. Ed., 1986, 25, 508-524), for example, in the presence of a palladium catalyst such as tetrakis(triphenylphosphine) palladium(0) or bis (triphenylphosphine)palladium(II) chloride, in a suitable solvent such as an ether, for example dioxane, or an aromatic hydrocarbon, for example, toluene, at an elevated temperature, and in the presence of catalysts such as LiCl and CuI. The reaction can be carried out for from 10 to 15 minutes at from 150° C. to 160° C. in a microwave.

During the reaction a protecting group such as trimethylsilylethoxymethyl may be present. The group can be inserted by reacting with its chloride in the presence of a strong base such as sodium hydroxide in a solvent such as tetrahydrofuran at about room temperature under an inert atmosphere. It can be removed by heating to about reflux with an acid such as hydrochloric acid in a solvent such as ethanol generally for about one hour.

Compounds of formula II can be made by reacting a compound of formula IV:

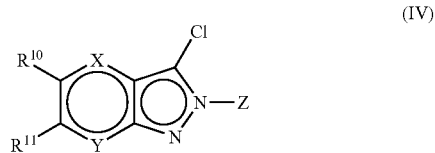

wherein X, Y and Z are as defined for formula I and $R^{10}$ and $R^{11}$ are as defined above, with a base such as potassium hydroxide in a solvent such as methanol generally at a temperature of about 150° C. in a microwave for about 15 minutes.

Compounds of formula IV can be made by reacting a compound of formula V:

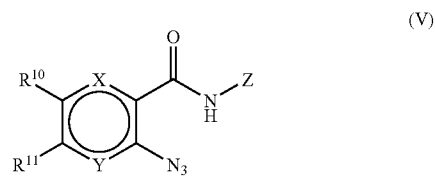

wherein X, Y and Z are as defined for formula I and $R^{10}$ and $R^{11}$ are as defined above with a ring closing agent such as thionyl chloride generally at reflux for about 24 hours.

Compounds of formula V can be made by reacting a compound of formula VI with a compound of formula VII:

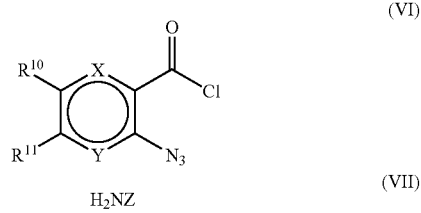

wherein X, Y and Z are as defined for formula I and $R^{10}$ and $R^{11}$ are is as defined above generally in the presence of a catalyst such as 4-dimethylaminopyridine in a solvent such as dichloromethane at about room temperature for one hour.

Compounds of formula VI can be made by reacting a compound of formula VIII:

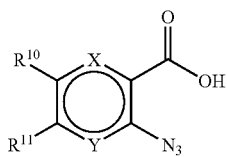

(VIII)

wherein X and Y are as defined for formula I and $R^{10}$ and $R^{11}$ are as defined above, with a chlorinating agent such as thionyl chloride generally at reflux for about two hours.

Compounds of formula VIII can be made by reacting a compound of formula IX:

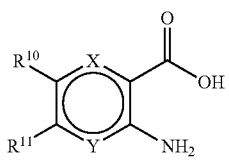

(IX)

wherein X and Y are as defined for formula I and $R^{10}$ and $R^{11}$ are as defined above first with a mixture of an acid such as hydrochloric acid and a nitrite such as sodium nitrite generally in a solvent such as water at about 5° C. and then with an azide such as sodium azide in the presence of a compound such as sodium acetate in a solvent such as water at about room temperature for about thirty minutes.

In an alternative process compounds of formula I can be made by reacting a compound of formula IV under conditions described above for a Suzuki or Stille coupling with a compound of formula III, followed by reaction with a base such as potassium hydroxide in a solvent such as methanol at about 160° C. for about 2 minutes in a microwave.

Compounds of formula I in which X is $CR^1$, Y is N, $R^{10}$ is $R^1$ and $R^{11}$ is W can also be made by reacting a compound of formula X with a formula of XI:

(X)

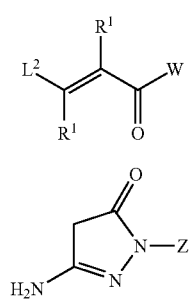

(XI)

in which $R^1$, W and Z are as defined for formula I and $L^2$ is a leaving group such as dimethylamino. The reaction is generally carried out in a solvent such as pyridine at about reflux for about three hours.

Compounds of formula XI can be made by reacting a compound of formula XII with a compound of formula XIII:

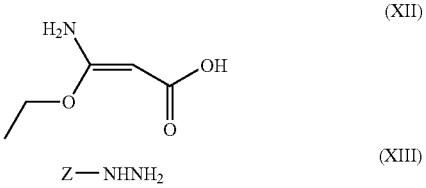

in which Z is as defined for formula I generally in a solvent such as toluene at about reflux for about one hour.

Compounds of formula XII can be made from a preceding ester by reacting with a mild base such as potassium carbonate in a solvent such as ether at about 0° C.

Compounds of formula I can be converted to other compounds of formula I by standard methods.

Where the synthesis of intermediates and starting materials is not described these compounds are commercially available or known in the literature or can be made from commercially available compounds or compounds known in the literature by standard methods.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The following Examples serve to illustrate the preparation of compounds of the present invention.

EXAMPLE 1

1,2-Dihydro-2-(4-trifluoromethylphenyl)-6-(3-trifluoromethyl-2-pyridinyl)-3H-indazol-3-one Step 1: 2-Azido-4-bromobenzoic acid To a solution of 2-amino-4-bromobenzoic acid (8.4 g, 0.039 mol) in a mixture of concentrated HCl (70 mL) and $H_2O$ (100 mL) was added a solution of $NaNO_2$ (2.8 g, 0.044 mol) in $H_2O$ (40 mL) such that the reaction temperature did not rise above 5° C. After addition was complete the resulting slurry was stirred for 15 min and the cold mixture added in aliquots to a solution of $NaN_3$ (2.5 g, 0.039 mol) and NaOAc (38 g, 0.47 mol) in $H_2O$ (80 mL) at room temperature. The resulting slurry was stirred for 30 min and the solid collected by filtration giving 6.4 g (68% yield) of product as a tan powder. $^1$H NMR (360 MHz, DMSO): 7.46 (1H, dd, J 1.4 and 7.5 Hz), 7.57 (1H, d, J 1.4 Hz), 7.70 (1H, d, J 7.5 Hz).

Step 2: 2-Azido-4-bromo-N-(4-trifluoromethylphenyl)-benzamide

The product of Step 1 (6.4 g, 0.026 mol) was heated in $SOCl_2$ (30 mL) at reflux for 2 h. The excess reagent was then evaporated and chased with toluene (2×10 mL). The residue was dissolved in dry $CH_2Cl_2$ (20 mL) and added dropwise to a solution of 4-(dimethylamino)pyridine (3.2 g, 0.026 mol) and 4-aminobenzotrifluoride (4.3 g, 0.026 mol) in $CH_2Cl_2$ (40 mL) cooled in ice. When addition was complete (10 min), the mixture was stirred and warmed to room temperature over 1 h, then washed with 2N HCl (15 mL), 2N $Na_2CO_3$ solution (15 mL), brine (10 mL), dried ($MgSO_4$) and concentrated to give 8.4 g (84% yield) of product as a buff solid. ¹H NMR (360 MHz, CDCl₃): 7.40 (1H, d, J 1.4 Hz), 7.44 (1H, dd, J 1.4 and 8.5 Hz), 7.63 (2H, d, J8.5 Hz), 7.80 (2H, d, J 8.5 Hz), 8.14 (1H, d, J 8.5 Hz).

Step 3: 6-Bromo-3-chloro-2-(4-trifluoromethylphenyl)-2H-indazole

A solution of the product of Step 2 (3 g, 0.0078 mol) in SOCl₂ (15 mL) was heated at reflux for 24 h. The mixture was then concentrated and the residue partitioned between ether (3×20 mL) and Na₂CO₃ solution (10 mL). The organic phase was separated, dried (MgSO₄) and concentrated to give 2.5 g (85% yield) of product as a tan powder. ¹H NMR (360 MHz, CDCl₃): 7.25 (1H, d, J 8.9 Hz), 7.37 (1H, d, 8.9 Hz), 7.80-7.95 (5H, m).

Step 4: 1,2-Dihydro-6-bromo-2-(4-trifluoromethylphenyl)-3H-indazol-3-one

A solution of the product of Step 3 (2.4 g, 0.0064 mol) in 1M KOH in MeOH (16 mL) was heated at 150° C. in a sealed tube via microwave irradiation for 15 min. The mixture was then concentrated, diluted with H₂O, acidified with 1N HCl and the resulting precipitate collected by filtration to give 1.0 g (44% yield) of product. ¹H NMR (360 MHz, CDCl₃): 7.37 (1H, dd, J 1.4 and 8.5 Hz), 7.66 (1H, d, 1.4 Hz), 7.73 (1H, d, 8.5 Hz), 7.89 (2H, d, 8.5 Hz), 8.13 (2H, d, 8.5 Hz), 11.0 (1H, s).

Step 5: 6-Bromo-1,2-dihydro-2-(4-trifluoromethylphenyl)-1-(2-trimethylsilyl ethoxymethyl)-3H-indazol-3-one A suspension of NaH in mineral oil (60%, 0.17 g, 0.0041 mol) was added portionwise to a solution of the product of Step 4 (1.3 g, 0.0035 mol) in dry THF (50 mL) at room temperature under N₂. After 20 min, SEM chloride (0.68 g, 0.0041 mol) in THF (15 mL) was added and the resulting slurry stirred at room temperature overnight. The mixture was quenched with brine (10 mL) and extracted into ether (3×20 mL). The organic phase was washed with 1N HCl (10 mL), 2N NaOH (10 mL), brine (10 mL), dried (MgSO₄) and concentrated to give crude product as an oil.

Step 6: 1,2-Dihydro-2-(4-trifluoromethylphenyl)-6-(3-trifluoromethyl-2-pyridinyl)-1-(2-(trimethylsilyl)ethoxymethyl)-3H-indazol-3-one The product of Step 5 (1.3 g, 2.6 mmol), was dissolved in dioxane (10 mL) and flushed with N₂. Bis(pinacolato)diboron (680 mg, 2.6 mmol), bis(diphenylphosphino)ferrocenyl palladium(II) dichloride (60 mg) and KOAc (380 mg, 3.9 mmol) were added. The mixture was stirred at 100° C. overnight. 2-Chloro-3-trifluoromethylpyridine (470 mg, 2.6 mmol), bis(diphenylphosphino)ferrocenyl palladium(II) dichloride (20 mg) and saturated Na₂CO₃ solution (1 mL) were added, and the mixture heated at reflux for a further 18 h. Purification by column chromatography gave 0.2 g of product as an oil.

MS: (ES (M+1)) 554.

Step 7: 1,2-Dihydro-2-(4-trifluoromethylphenyl)-6-(3-trifluoromethyl-2-pyridinyl)-3H-indazol-3-one The product of Step 6 (0.2 g), in a mixture of concentrated HCl (2 mL) and EtOH (3 mL), was heated at reflux for 1 h. The mixture was concentrated and the residue crystallized from EtOH/H₂O to give 70 mg of product as a colourless solid. ¹H NMR (360 MHz, CDCl₃): 7.33 (1H, s), 7.39 (1H, d, J 8.0 Hz), 7.43 (1H, s), 7.5-7.55 (1H, m), 7.73 (2H, d, J 8.0 Hz), 7.99 (1H, d, J 8.0 Hz), 8.09 (2H, d, J 8.0 Hz), 8.14 (1H, d, J 8.0 Hz), 8.9 (1H, d, J 8.0 Hz).

EXAMPLE 2

1,2-Dihydro-6-(3-methyl-2-pyridinyl)-2-(4-trifluoromethylphenyl)-3H-indazol-3-one The product of Example 1, Step 4 (0.35 g, 1 mmol)), bis(diphenylphosphino) ferrocenyl palladium(II) dichloride 0) (40 mg), CuI (19 mg, 0.1 mmol), LiCl (126 mg, 3 mmol), 3-methyl-2-(tri-ⁿbutylstannyl)pyridine (530 mg, 1.4 mmol) and dioxane (4 mL) were heated at 150° C. for 15 min under microwave irradiation. The resulting mixture was purified by column chromatography (silica; EtAc:hexane 1:2->EtAc) to give 0.2 g (54%) of the title compound as a colourless solid. ¹H NMR (360 MHz, DMSO): 2.5 (3H, s), 7.30-7.40 (2H, m), 7.50 (1H, m), 7.78 (1H, d, J 7.7 Hz), 7.85 (1H, d, J 8.0 Hz), 7.90 (2H, d, J 8.5 Hz), 8.19 (2H, d, J 8.5 Hz), 8.53 (1H, d, J 4.6 Hz), 10.8 (1H, s).

EXAMPLE 3

1,2-Dihydro-2-(4-trifluoromethylphenyl)-5-(3-trifluoromethyl-2-pyridinyl)-3H-indazol-3-one This compound was prepared as described for Example 1 replacing 2-azido-4-bromobenzoic acid with 2-azido-5-bromobenzoic acid in Step 2. ¹H NMR (360 MHz, DMSO): 7.52 (1H, d, J 8.0 Hz), 7.65-7.75 (1H, m), 7.76 (1H, dd, J 1.2 and 8.0 Hz), 7.83 (1H, s), 7.91 (2H, d, J 8.0 Hz), 8.18 (2H, d, J 8.0 Hz), 8.34 (1H, d, J 8.0 Hz), 8.9 (1H, d, J 8.0 Hz), 11.1 (1H, s).

EXAMPLE 4

1,2-Dihydro-6-(2-methoxyphenyl)-2-(4-trifluoromethylphenyl)-3H-indazol-3-one

Step 1: 3-chloro-6-(2-methoxyphenyl)-2-(4-trifluoromethylphenyl)-2H-indazole

A mixture of the product of Example 1 Step 3 (100 mg, 0.26 mmol), 2-methoxyphenylboronic acid (50 mg, 0.33 mmol), bis(diphenylphosphino)ferrocenyl palladium(II) dichloride 0) (20 mg), saturated Na₂CO3 solution (1 mL) and dioxane (2 mL) was heated at 160° C. for 10 min via microwave irradiation. The title product was then purified by preparative thin layer chromatography on silica eluting with EtAc:hexanes 1:5. MS: (ES (M+1)) 403,405.

Step 2: 1,2-Dihydro-6-(2-methoxyphenyl)-2-(4-trifluoromethylphenyl)-3H-indazol-3-one The product of Step 1 (100 mg) was dissolved in 1N KOH in MeOH (2 mL) and heated at 160° C. for 2 min via microwave irradiation. The resulting yellow solution was concentrated, diluted with water and acidified with 2N HCl. The precipitate was collected and recrystallised from EtOH/H₂O to give 21 mg of product as colourless needles. ¹H NMR (500 MHz, DMSO): 3.81 (3H, s), 7.08 (1H, t, J 7.4 Hz), 7.18 (1H, d J 7.4 Hz), 7.31 (1H, dd, J 1.2 and 8.0 Hz), 7.38 (1H, dd, J 1.2 and 8.0 Hz), 7.39-7.42 (1H, m), 7.44 (1H, s), 7.79 (1H, d, J 8.0 Hz). 7.89 (2H, d, J 8.5 Hz), 8.18 (2H, d, J 8.5 Hz), 10.76 (1H, s).

EXAMPLE 5

1,2-Dihydro-6-(3-methyl-2-pyridinyl)-2-(4-trifluoromethylphenyl)-3H-pyrazolo[3,4-b]pyridin-3-one Step 1: 5-Amino-2,4-dihydro-2-(4-trifluoromethylphenyl)-3H-pyrazol-3-one Ethyl 3-amino-3-ethoxy-2-propenoate hydrochloride (10 g, 0.05 mol) was added to a mixture of 40% aqueous K₂CO₃

(70 mL) and ether (50 mL) cooled in ice. The organic phase was extracted with ether (2×50 mL) and the extracts dried ($K_2CO_3$) and concentrated to give 7 g of a gummy solid. A solution of 4-trifluoromethylphenylhydrazine (7.7 g, 0.043 mol) in toluene (50 mL) was added and the mixture heated at reflux for 1 h. The mixture was concentrated and the residue treated with a freshly prepared NaOEt in EtOH (Na (1.9 g, 0.082 mol), EtOH (50 mL)) and heated at reflux for 1 h. After concentration the residue was partitioned between ether (2×30 mL) and $H_2O$ (50 mL). The aqueous phase was acidified and re-extracted with ether to give 6.0 g of product as an orange solid. $^1$H NMR (360 MHz, $CDCl_3$): 3.5 (2H, s), 4.5 (2H, s), 7.60 (2H, d, J 8.5 Hz), 8.00 (2H, d, J 8.5 Hz).

Step 2: 1,2-Dihydro-6-(3-methyl-2-pyridinyl)-2-(4-trifluoromethylphenyl)-3H-pyrazolo[3,4-b]pyridin-3-one A mixture of the product of Step 1 (1.68 g, 0.0074 mol) and 3-(dimethylamino)-1-(3-methyl-2-pyridinyl)-2-propen-1-one (EP-A-0233461) (1.4 g, 0.0074 mol) in pyridine (20 mL) was heated at reflux for 3 h. The mixture was concentrated and then triturated to give a solid which was recrystallised from iPrOH to give 0.64 g (23% yield) of product as a yellow powder. $^1$H NMR (360 MHz, DMSO): 2.6 (3H, s), 7.45-7.55 (1H, m), 7.55-7.65 (1H, m), 7.85-7.95 (3H, m), 8.20 (2H, d, J 8.5 Hz), 8.39 (1H, d, J 8.0 Hz), 8.61 (1H, d, J 4.6 Hz).

The above exemplified compounds of the present invention have been tested in the following assay and generally possess an $IC_{50} < 0.5$ μM and, in the majority of cases, <200 nM.

Biological Methodology

Determination of in vitro Activity

CHO cells, stably expressing recombinant human VR1 receptors and plated into black-sided 384-well plates, were washed twice with assay buffer (Hepes-buffered saline) and then incubated with 1 uM Fluo-3-AM for 60 minutes in darkness. Cells were washed twice more to remove excess dye, before being placed, along with plates containing capsaicin and test compounds in a Molecular Devices FLIPR. The FLIPR simultaneously performed automated pharmacological additions and recorded fluorescence emmission from Fluo-3. In all experiments, basal fluorescence was recorded, before addition of test compounds and subsequent addition of a previously determined concentration of capsaicin that evoked 80% of the maximum response. Inhibition of capsaicin evoked increases in intracellular $[Ca^{2+}]$ were expressed relative to wells on the same plate to which capcaicin was added in the absence of test compounds. Increases in intracellular $[Ca^{2+}]$ occuring after addition of test compound alone, prior to addition of capsaicin, allow determination of intrinsic agonist or partial agonist activity, if present.

The invention claimed is:

1. A compound of formula (I):

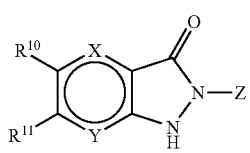

(I)

wherein X and Y are each $CR^1$ or N;
one of $R^{10}$ and $R^{11}$ is $R^1$ and the other is W;
each $R^1$ is hydrogen, halogen, hydroxy, cyano, amino, $C_{1-4}$alkyl, $C_{1-4}$alkoxy, halo$C_{1-4}$alkyl or halo$C_{1-4}$alkoxy;
W is a phenyl ring or a six-membered heteroaromatic ring containing one, two or three nitrogen atoms, which ring is optionally substituted by halogen, $C_{1-6}$alkyl, $C_{2-6}$alkenyl, $C_{2-6}$alkynyl, $C_{1-6}$alkoxy, cyano, nitro, amino, $C_{1-6}$alkylamino, di($C_{1-6}$alkyl)amino, halo$C_{1-6}$alkyl, halo$C_{1-6}$alkoxy, carboxy, hydroxy$C_{1-6}$alkyl or amino-$C_{1-6}$alkyl; and
Z is a phenyl ring or a six-membered heteroaromatic ring containing one, two or three nitrogen atoms, which ring is substituted at least at the position para to the attachment of the ring to the rest of the molecule by halogen, $C_{1-6}$alkyl, $C_{2-6}$alkenyl, $C_{2-6}$alkynyl, $C_{1-6}$alkoxy, cyano, nitro, amino, $C_{1-6}$alkylamino, di($C_{1-6}$alkyl)amino, halo$C_{1-6}$alkyl, halo$C_{1-6}$alkoxy, carboxy, hydroxy-$C_{1-6}$alkyl or amino$C_{1-6}$alkyl;
or a pharmaceutically acceptable salt thereof.

2. A compound of claim 1 represented by formula (IA);

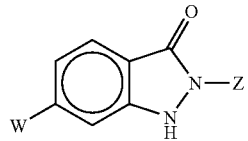

(IA)

wherein W is phenyl or pyridyl optionally substituted by halogen, $C_{1-2}$alkyl, $C_{1-2}$alkoxy, halo$C_{1-2}$alkyl or halo-$C_{1-2}$alkoxy; and
Z is phenyl or pyridyl substituted at the position para to the point of attachment to the rest of the molecule by halogen, $C_{1-2}$alkyl, $C_{1-2}$alkoxy, halo$C_{1-2}$alkyl or halo-$C_{1-2}$alkoxy;
or a pharmaceutically acceptable salt thereof.

3. A compound selected from:
1,2-dihydro-2-(4-trifluoromethylphenyl)-6-(3-trifluoromethyl-2-pyridinyl)-3H-indazol-3-one;
1,2-dihydro-6-(3-methyl-2-pyridinyl)-2-(4trifluoromethylphenyl)-3H-indazol-3-one;
1,2-dihydro-2-(4-trifluoromethylphenyl)-5-(3-trifluoromethyl-2-pyridinyl)-3H-indazol-3-one;
1,2-dihydro-6-(2-methoxyphenyl)-2-(4-trifluoromethylphenyl)-3H-indazol-3-one; and
1,2-dihydro-6-(3-methyl-2-pyridinyl)-2-(4-trifluoromethylphenyl)-3H-pyrazolo[3,4-b]pyridin-3-one;
or a pharmaceutically acceptable salt thereof.

4. A pharmaceutical composition comprising a compounds of claims 1, or pharmaceutically acceptable salts thereof in association with a pharmaceutically acceptable carrier or excipient.

5. A method for treating a disease or condition in which pain and/or inflammation predominates comprising administering a compound of claim 1, or a composition comprising a compound of claim 1 or a pharmaceutically acceptable salt thereof.

* * * * *